(12) United States Patent
Peer et al.

(10) Patent No.: US 6,315,769 B1
(45) Date of Patent: Nov. 13, 2001

(54) APPARATUS AND METHOD FOR MEASURING THE AMOUNT OF FLUID CONTAINED IN AN IMPLANTABLE MEDICAL DEVICE

(75) Inventors: Twan Peer, Landgraaf; Arnoldus Bakels, Simpleveld, both of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/394,354

(22) Filed: Sep. 13, 1999

(51) Int. Cl.[7] ................................................. A61K 9/32
(52) U.S. Cl. .................... 604/891.1; 604/502; 604/132
(58) Field of Search ............................. 604/890.1–892.1, 604/65, 66, 93.01, 132, 133, 141, 150, 151, 153, 154, 288.01, 502, 505; 128/DIG. 12, DIG. 13, 903

(56) References Cited

U.S. PATENT DOCUMENTS

| | | |
|---|---|---|
| 4,482,346 | * 11/1984 | Reinicke ............................ 604/152 |
| 5,328,460 | 7/1994 | Lord et al. . |
| 5,443,450 | 8/1995 | Kratoska et al. . |
| 5,643,207 | 7/1997 | Rise . |
| 6,152,898 | * 11/2000 | Olsen ............................. 604/132 X |
| 6,228,050 | * 5/2001 | Olsen et al. ....................... 604/93.01 |

\* cited by examiner

Primary Examiner—Anhtuan T. Nguyen
(74) Attorney, Agent, or Firm—Thomas F. Woods; Thomas G. Berry

(57) ABSTRACT

An implantable pump apparatus and method of operating the implantable pump for infusing a fluid into a body are described. The implantable pump apparatus includes a support member. A pressure sensitive resistor member is disposed on a first side of the support member. A spring member includes a first end which is adjacent to the pressure sensitive resistor member. An expandable fluid reservoir member includes a first end which is adjacent to a second end of the spring member. The level of fluid within the expandable fluid reservoir member is determined by measuring a force applied to the pressure sensitive resistor member.

12 Claims, 3 Drawing Sheets

APPARATUS AND METHOD FOR MEASURING THE AMOUNT OF FLUID CONTAINED IN AN IMPLANTABLE MEDICAL DEVICE

FIELD OF THE INVENTION

The present invention relates to implantable medical devices and associated pumps for infusing a fluid into a body, and the methods and construction of such devices. Additionally, the present invention concerns the means by which an implantable medical device and the pump or drug reservoir contained within it measures the amount of fluid contained therein.

BACKGROUND OF THE INVENTION

The use of implantable fluid medication dispensers is presently well known in the art. Examples of implantable fluid medication dispensers are contained within U.S. Pat. Nos. 5,328,460, 5,443,450 and 5,643,207. Such dispensers are used to dispense a specified amount of medication into a patient's body, and may, for example, deliver low doses of morphine into a patient's body to treat cancer pain.

Implantable fluid medication dispensers typically include an internal fluid medication reservoir for receiving, storing and dispensing a supply of a fluid medication. Such a reservoir is generally included within a housing of some shape or form that may be implanted in the body. Other components of such a device include a power source (such as a battery), a mechanism for pumping the fluid medication into the patient's body, and a programmable mechanism to assist in dispensing the fluid medication according to a predetermined schedule.

Because those fluid medication dispensers are implanted within a patient's body, they must in general be periodically replenished with medication. As a result, implantable fluid medication dispensers may include some means to replenish the fluid medication within the reservoir. U.S. Pat. No. 5,443,450 to Kratoska et al. discloses a typical reservoir refill assembly. Unfortunately, determining the level of medication contained within a fluid medication dispenser has proved to be problematic. At present, the absence of a fluid medication being dispensed to a patient is generally detected by physiological measures. Such measures may include symptoms associated with the malady to which the fluid medication is directed to prevent or abate.

There exists, therefore, a significant need for improvement in the measuring abilities of such implantable medication dispensers. Instead of relying upon symptomatic factors to determine when an implantable fluid medication device is in need of a replenishment of fluid which may cause unwarranted pain to the patient, it would be desirable to provide a means to determine the amount of fluid remaining in another more efficacious manner. The present invention fulfills at least some of these needs and provides further advantages.

Disclosures relating to implantable medication dispensers include the U.S. Patents listed below in Table 1.

TABLE 1

| Prior Art, U.S. patents. | | |
|---|---|---|
| 5,328,460 | July, 1994 | Lord, et al. |
| 5,443,450 | August, 1995 | Kratoska, et al. |
| 5,643,207 | July, 1997 | Rise |

As those of ordinary skill in the art will appreciate readily upon reading the Summary of the Invention, Detailed Description of the Preferred Embodiments and Claims set forth below, at least some of the devices and methods disclosed in the patents contained within Table 1 may be modified advantageously by using the teachings of the present invention.

SUMMARY OF THE INVENTION

The present invention overcomes at least some of the disadvantages of the prior art by providing a method of and apparatus for measuring the level of a fluid medication within an implantable pump apparatus and fluid medication dispenser, and by providing a structure that improves same.

The present invention has certain objects. That is, various embodiments of the present invention provide solutions to at least some of the problems existing in the prior art respecting the measurement of the amount of fluid remaining in an implantable medication dispenser, such as one or more of:

(a) difficulty in providing an accurate measurement of the amount of fluid medication remaining within the implantable pump apparatus;

(b) the inability to provide an accurate diagnosis concerning the amount of fluid medication remaining within an implantable pump apparatus without relying on physiological factors or symptoms of a patient; and (c) the inability to provide a safe and nonintrusive means to measure the amount of fluid medication remaining within an implantable pump apparatus without causing harm to a patient;

(d) basing the requirement of additional fluid medication on the detection of physiological factors;

(e) basing the requirement of additional fluid medication on a patient's symptoms; and (f) basing the requirement of additional fluid medication on other inaccurate and potentially unsafe methods.

The present invention provides solutions to at least some of the foregoing problems.

Various embodiments of the present invention provide one or more of the following advantages:

(a) providing an accurate indication of the amount of fluid remaining within an implantable fluid medication dispenser;

(b) providing a safe manner in which the amount of fluid remaining within an implantable fluid medication dispenser is measured;

(c) providing a manner in which the amount of fluid remaining within an implantable fluid medication dispenser is measured without relying on physiological factors of the patient;

(d) providing a manner in which the amount of fluid remaining within an implantable fluid medication dispenser is measured without relying on symptoms of the patient; and (e) providing a manner in which the amount of fluid remaining within an implantable fluid medication dispenser is measured without relying on other inaccurate and potentially unsafe methods.

Some embodiments of the present invention have certain features relating to the measurement of a fluid medication contained within an implantable fluid medication dispenser, including one or more of:

(a) an expandable reservoir for receiving a specified amount of a fluid medication that is situated within an enclosure;

(b) a pressure sensitive resistor attached to the bottom of the enclosure; and (c) a spring situated between the reservoir and the resistor for translating the displacement of the reservoir to a force applied to the spring.

BRIEF DESCRIPTION OF THE DRAWINGS

The foregoing and other advantages and features of the present invention will become apparent upon reading the following Detailed Description and referring to the accompanying Drawings in which like numbers refer to like parts throughout, and in which.

DETAILED DESCRIPTION OF THE PREFERRED EMBODIMENTS

Figure 1:
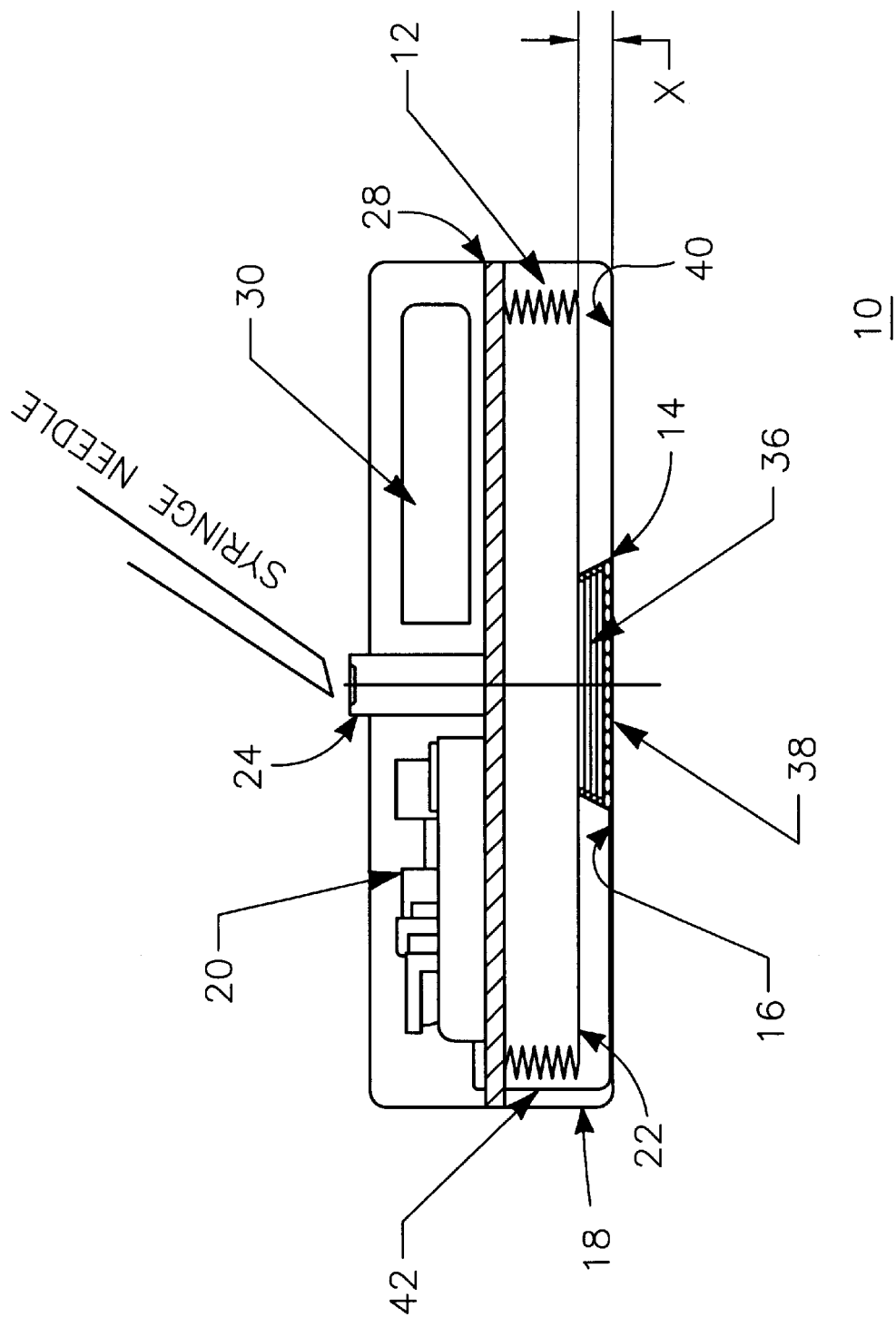
FIG. 1 shows a cross-sectional view of the internal components of one embodiment of an implantable pump apparatus of the present invention.
Figures 2, 3:
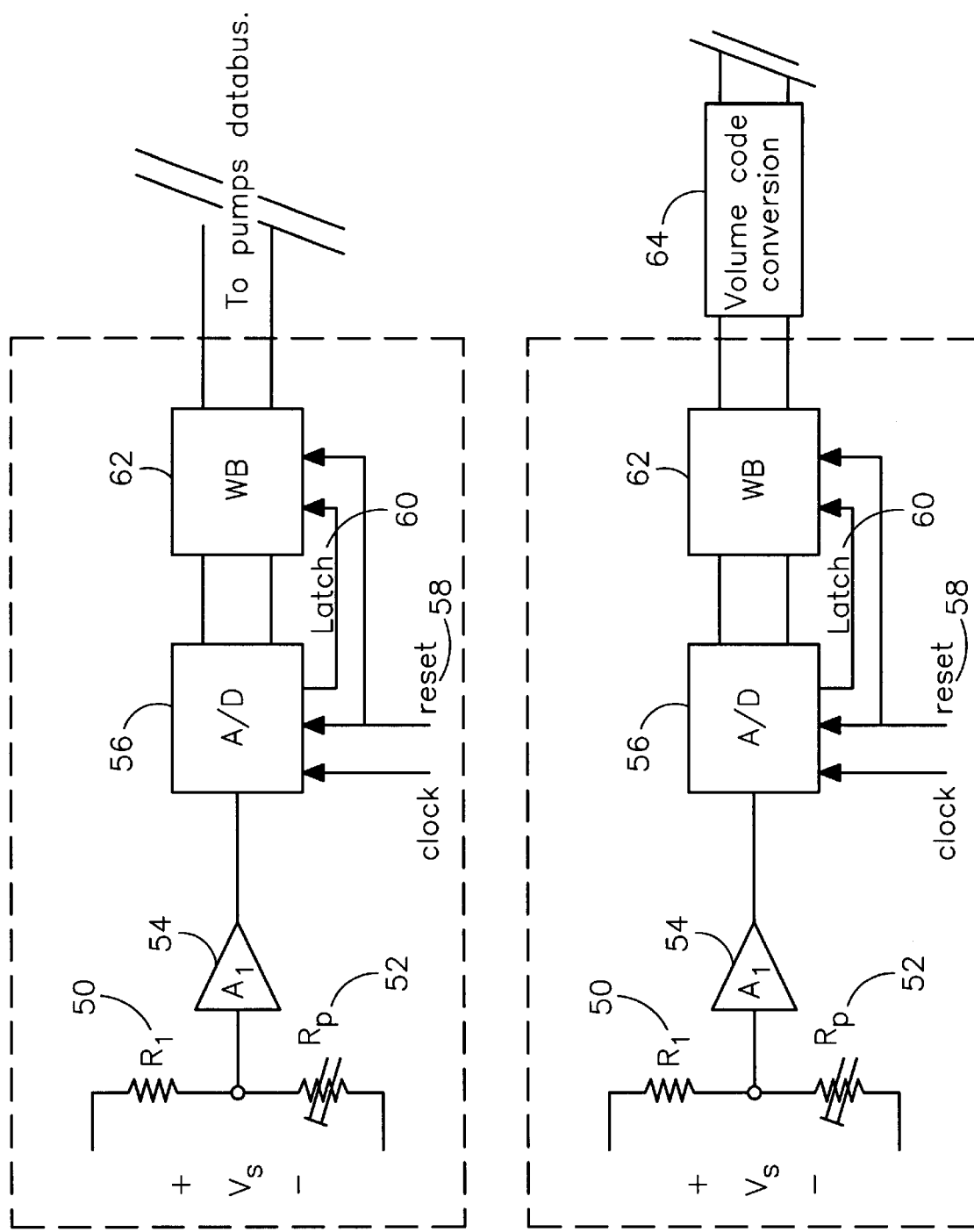
FIGS. 2 and 3 shows schematic views of two preferred embodiments of an electronic control circuit of the implantable pump apparatus of FIG. 1.

FIG. 1 shows a cross-sectional view of the components of one embodiment of implantable pump apparatus 10 made in accordance with the present invention. FIGS. 2 and 3 show diagrams of two preferred embodiments of an electronic control circuit 20 of the implantable pump apparatus of FIG. 1.

Implantable pump apparatus 10 of FIGS. 1–3 comprises expandable fluid reservoir member 12, support member 14, pressure sensitive resistor member 16 and spring member 36. Implantable pump apparatus 10 also includes a housing member 18 and electronic control circuit 20.

Support member 14 is shown in FIG. 1 as a portion of housing member 18. Support member 14 provides a base on which pressure sensitive resistor member 16 may be placed. In other words, it provides a platform on which expandable fluid reservoir member 12 may, due to the amount of fluid contained within, exert a displacement upon pressure sensitive resistor member 16. This displacement is first converted into a force, and then ultimately into an indication signal corresponding to the amount of fluid contained within expandable fluid reservoir member 12. As is the case with housing member 18, as described below, the support member 14 may be formed of one or more of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof.

Pressure sensitive resistor member 16 of implantable pump apparatus 10 is disposed on first side 40 of support member 14. Pressure sensitive resistor member 16 may preferably be any typical type of resistor presently known in the art having the ability to detect and measure a force applied against itself. As a result, pressure sensitive resistor member 16 preferably maintains a reading of the force applied to it from spring member 36, which, as explained in more detail below, is translated from the displacement of expandable fluid reservoir member 12. Furthermore, the reading of the force value maybe directed to electronic control circuit 20 by means of connection wires or flexitape (shown at element 42 in FIG. 1).

Spring member 36 of implantable pump apparatus 10 is disposed between expandable fluid reservoir member 12 and pressure sensitive resistor member 16. Preferably, spring member 36 may be formed of one or more of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof. Spring member 36 translates the displacement of expandable fluid reservoir member 12 into a force, which is then applied to pressure sensitive resistor member 16. Additionally, spring member 36 ensures that expandable fluid reservoir member 12 operably contacts pressure sensitive resistor member 16 when there is any level of fluid contained within expandable fluid reservoir member 12. As a result, such continuous contact ensures that pressure sensitive resistor member 16 may continuously translate the displacement of expandable fluid reservoir member 12, as described above, in an effort to provide a reading corresponding to the level of fluid contained within expandable fluid reservoir member 12.

Expandable fluid reservoir member 12, which is preferably disposed within housing member 18, further includes first end 28, second end 22, inlet 24 and an outlet (not shown). Expandable fluid reservoir member 12 receives an amount of fluid medication (illustrated by Step 100 in FIG. 4) through inlet 24. Additionally, expandable fluid reservoir member 12 dispenses a predetermined amount of fluid medication through an outlet (illustrated by Step 200 in FIG. 4 and not shown). The outlet may be similar to that shown in U.S. Pat. No. 5,443,450 to Kratoska et al.

Expandable fluid reservoir member 12 is preferably made of a biocompatible, biostable material. For example, expandable fluid reservoir member 12 may be formed of one or more of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof.

Similar to expandable fluid reservoir member 12, first end 28 may also be formed of one or more of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof. A first side of first end 28 of expandable fluid reservoir member 12 supports electronic control circuit 20 of implantable pump apparatus 10. Additionally, the first side of first end 28 may support the battery and pumping member 30 of implantable pump apparatus 10.

Electronic control circuit 20 preferably comprises a typical electronic circuit, presently known in the art, which determines the level of fluid contained within expandable fluid reservoir member 12. Preferably, electronic control circuit 20 accomplishes this function by acquiring a signal corresponding to the force applied at pressure sensitive resistor member 16 of implantable pump apparatus 10

Figure 4:
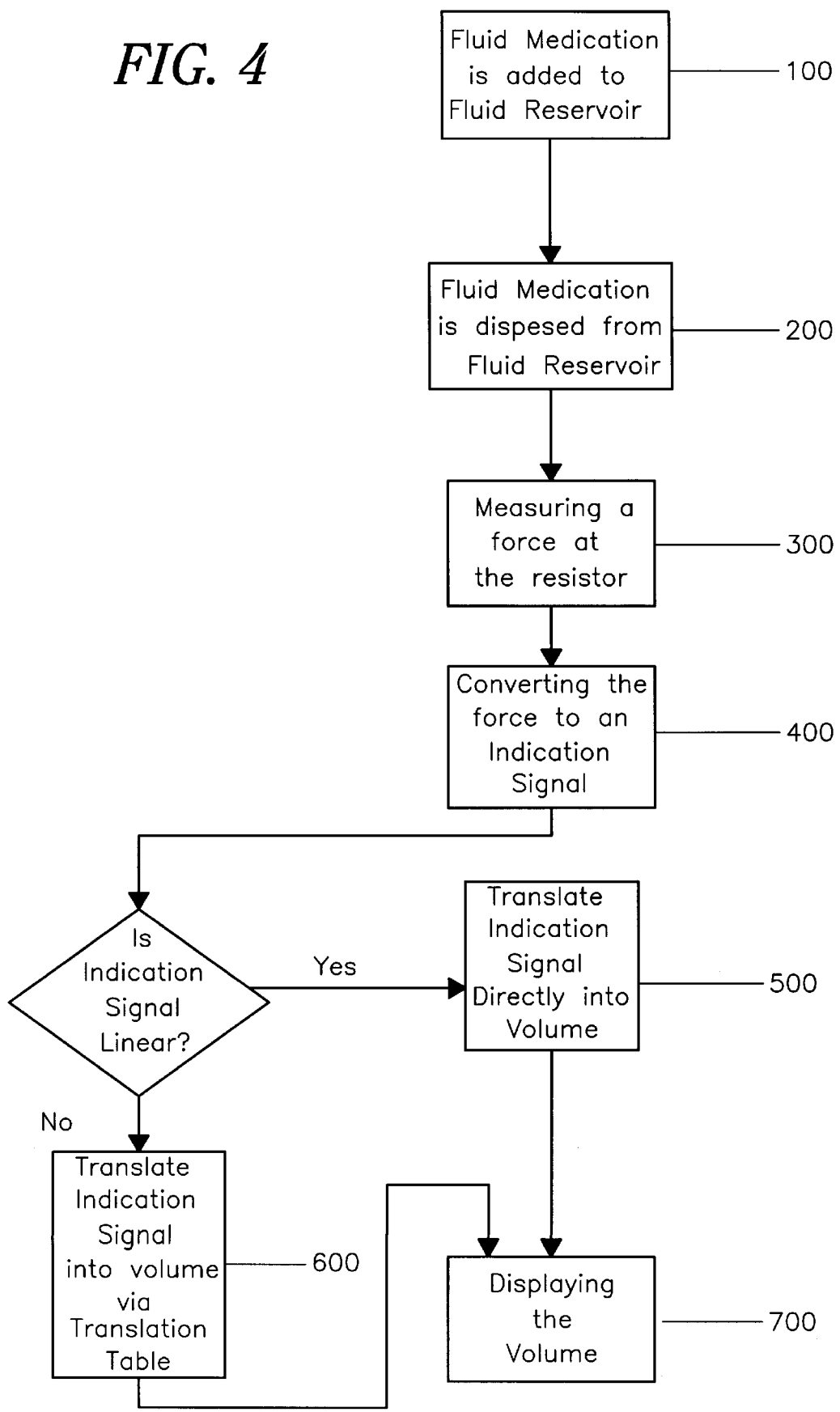
FIG. 4 shows a block diagram of one embodiment of one method of the present invention for measuring a fluid contained within an implantable pump apparatus.

(illustrated at Step 300 of FIG. 4). After receiving the signal corresponding to the applied force, electronic control circuit 20 preferably converts the measured force value into an indication signal corresponding to the level of fluid remaining within expandable fluid reservoir member 12 (see step 400 of FIG. 4). In other words, the level of fluid is measured by correlating a face value received at pressure sensitive resistor member 16 of implantable pump apparatus 10 with a fluid level. The force value received at pressure sensitive resistor member 16 of implantable pump apparatus 10 is proportional to and correlates with the pressure exerted on spring member 36 from partially or fully expanded expandable fluid reservoir member 12.

By way of example only, the conversion of the force value to an indication signal may be accomplished by means of computer programmable software located within electronic control circuit 20. A table stored in memory compares the received force value with a corresponding level of fluid. Alternatively, the conversion may occur by means of a different method which takes into account such factors as the sensed force value, the weight (or mass) of an amount of medication, and the like. Furthermore, the conversion may be realized by any other suitable computing or translation means used to arrive at a volumetric or linear value corresponding to the volume or level of fluid contained within expandable fluid reservoir member 12. In one embodiment of the invention, the force applied to spring member 36 determines a resistance value at pressure sensitive resistor member 16 which is in turn sensed and converted to a fluid level.

Electronic control circuit 20 preferably includes means for computing capable of performing the calculations required to determine the amount of fluid remaining in reservoir member 12, and also preferably includes means for storing data representative of such volume. Suitable computing and data storing means include micro-processors, micro-computers, CPUs and the like, and their associated A/D converters, D/A converters, RAM, ROM, EEPROM memory, and so on.

Turning now to FIG. 2, a more detailed description of electronic control circuit 20 follows. Resistor $R_1$ (50) determines the resistance value of the current range through the combination of $R_1$ and $R_P$ (52—the resistance value measured at pressure sensitive resistor member 16). A stabilized voltage $V_S$ feeds the circuit. The value of the voltage at the junction of $R_1$ and $R_P$ is determined. Amplifier, $A_1$ (54) then buffers the resultant voltage value. The buffered output voltage value of $A_1$ is then fed into an analog-to-digital converter(A/D, 56) which translates the analog buffered output voltage value at the A/D input into a digital count, or word, with a certain bit width. A/D 56 is further controlled by reset signal 58 generated by known circuitry thereby controlling data traffic in the electronic portions of the battery and pumping member 30. Latch signal 60 directs a word buffer (62, WB) to store the result of the conversion. The digital count or word may have, for example, a 12 or 16 bit width, or it may have a lesser bit width, depending on the accuracy needed for the measured volume.

If all the above-mentioned components operate within a linear range, then the digital count or word may be translated directly into a volume reading which corresponds directly to the amount of fluid remaining within expandable fluid reservoir member 12 (illustrated at Step 500 of FIG. 4). For example, if spring member 16 translates the displacement of expandable fluid reservoir member 12 into a linear force value, and if the linear force value is translated linearly into a resistance value, and finally if the shape of expandable fluid reservoir member 12 translates linearly into a volumetric reading, then the components cooperate in linear fashion.

If, however, the above-described relationships are non linear, then a translation table or the like may be required to translate the digital count or word value accurately into a corresponding measurement of volume (illustrated at Step 600 of FIG. 4). This translation may be done via code table 64, which may be contained within electronic control circuit 20 in which the characteristic volume of the tank may be coded. Alternatively, the translation into volume may occur in any other similar manner in which an accurate reading of the volume of the expandable fluid reservoir member 12 may be realized. Such non-linear translation is illustrated in FIG. 3.

Regardless of the translation method utilized, and returning to FIG. 1, electronic control circuit 20 may be telemetrically, electromagnetically and/or RF coupled to an external device using devices and methods well known in the art. The external device may include a display device which receives and displays the indication signal corresponding to the level of fluid remaining within the expandable fluid reservoir member 12 of implantable pump apparatus 10 (illustrated at Step 700 of FIG. 4). Preferably, the display device is a digital display of the level of fluid in expandable fluid reservoir member 12. However, the display device may comprise any other suitable display means that will accurately portray the level of fluid, such as, for example, an analog display, a Liquid Crystal Display, a Light-Emitting Diode display, etc.

Battery and pumping member 30 preferably includes a means by which implantable pump apparatus 10 may be powered or operated.

Preferably, such a means employs a low voltage Direct Current battery. An example of this type of electrical power device is a watch battery or other suitable type of miniaturized electrochemical cell, capacitor or the like well known in the art.

Additionally, battery and pumping member 30 may include a means by which the fluid contained within expandable fluid reservoir member 12 may be directed into the body of the patient. Preferably, such a means may include a control means by which the dispensing of the fluid medication is regulated and controlled to occur at certain predetermined intervals or rates such that a predetermined amount of fluid medication is controllably dispersed in the patient's body. For example, a computer may be programmed to permit 5 ml of fluid medication to be dispensed into the patient's body at 6-hour. Similar to expandable fluid reservoir member 12, the housing and other portions of battery and pumping member 30 may be formed of one or more of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof.

Inlet 24 is preferably disposed on the first side of first end 28 of implantable pump apparatus 10. Inlet 24 is configured to receive fluid that is to be contained within expandable fluid reservoir member 12 (Step 100 of FIG. 4). Preferably, the fluid may be injected into expandable fluid reservoir member 12 via inlet 24 by means of a syringe as shown in the Figures. Alternatively, the fluid may be injected into member 12 by any other suitable means, such as by pump means. Therefore, inlet 24 may be a female receptor configured to receive a syringe or a pump connection.

Additionally, inlet 24 may be an inlet configured to allow the infusion of fluid medication into member 12, but that does not permit the dispensation of such medication. Thus, inlet 24 may be a check valve that permits inflow but not outflow of fluid medication.

An outlet (not shown) acts conversely to inlet 24. That is, the outlet provides a means through which the fluid contained within expandable fluid reservoir member 12 may be infused into the body as illustrated at Step 200 of FIG. 4. Preferably, the outlet may be regulated by means of a control device that monitors and controls in a predetermined fashion the amount of fluid permitted to enter the body.

Transfer member 38 is preferably positioned between spring member 36 and pressure sensitive resistor member 16. Transfer member 38 evenly applies the force from spring member 36 to pressure sensitive resistor member 16. Transfer member 38 generally assumes the form of a flat washer but may be formed into any other suitable shape. Additionally, transfer member 38 may be formed of one or more of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof.

Housing member 18 of implantable pump apparatus 10 preferably encases expandable fluid reservoir member 12. Housing member 18 may protect expandable fluid reservoir member 12 and the body in which expandable fluid reservoir member 12 is implanted. Housing member 18 may be formed of one or more of niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof.

Although only a few exemplary embodiments of the present invention have been described in detail above, those skilled in the art will appreciate readily that many modifications are possible in the exemplary embodiments without materially departing from the novel teachings and advantages of the present invention. Accordingly, all such modifications are intended to be included within the scope of the present invention as defined in the following claims.

The scope of the present invention is not in any way limited to pumping devices and applications, but extends to other similar medical devices and methods. Additionally, the scope of the present invention is not in any way limited to applications in which a human body is infused with a fluid, but includes similar applications in other mammalians and mammalian organs.

The preceding specific embodiments are illustrative of the practice of the present invention. It is to be understood, therefore, that other expedients known to those skilled in the art or disclosed herein, may be employed without departing from the present invention or the scope of the appended claims.

In the claims, means-plus-function clauses are intended to cover the structures described herein as performing the recited function and not only structural equivalents, but also equivalent structure. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents listed in Table 1, or elsewhere hereinabove, are hereby incorporated by reference into the specification hereof, each in its respective entirety.

We claim:

1. A method of measuring the amount of a fluid present within an implantable pump while implanted within a body, comprising the steps of:

providing a support member, a pressure sensitive resistor member disposed on a first side of the support member, a spring member including a first end adjacent to the pressure sensitive resistor member, an expandable fluid reservoir member including a first end adjacent to a second end of the spring member;

adding the fluid to the expandable fluid reservoir member;

dispensing a portion of the fluid from the expandable fluid reservoir member; and measuring a force at the pressure sensitive resistor member.

2. The method of claim 1, wherein the force being applied to the pressure sensitive resistor member is applied from the expandable fluid reservoir member through the spring member.

3. The method of claim 2, further comprising converting the force to an indication signal.

4. The method of claim 3, further comprising providing an analog-to-digital convertor and converting the indication signal to a digital representation thereof.

5. The method of claim 4, further comprising transferring the digital representation to an external device.

6. The method of claim 3, further comprising providing means for computing and further comprising converting the indication signal into data representative of a volume corresponding to the volume of fluid within the expandable fluid reservoir member.

7. The method of claim 2, further comprising a transfer member disposed between the pressure sensitive resistor member and the spring member, and further comprising configuring the transfer member to evenly apply the force from the spring member to the pressure sensitive resistor member.

8. The method of claim 1, further comprising disposing the expandable fluid reservoir member within the housing member.

9. The method of claim 8, wherein the housing member is made of a niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof.

10. The method of claim 1, wherein the expandable fluid reservoir member is made of a niobium, titanium, titanium alloys such as titanium-6A1-4V or titanium-vanadium, platinum, molybdenum, zirconium, tantalum, vanadium, tungsten, iridium, rhodium, rhenium, osmium, ruthenium, palladium, silver, and/or alloys, mixtures and/or combinations thereof.

11. The method of claim 1, wherein the expandable fluid reservoir member further includes an inlet, and the method further comprises receiving the fluid from an outside source into the inlet.

12. The method of claim 1, wherein the expandable fluid reservoir member further includes an outlet, and the method further comprises dispensing the fluid from the outlet into the body.

* * * * *